(12) United States Patent
Brunner et al.

(10) Patent No.: US 9,113,818 B2
(45) Date of Patent: Aug. 25, 2015

(54) PRESSURE MEASURING SYSTEM, PRESSURE MEASURING SENSOR ASSEMBLY AND A METHOD OF MEASURING A PRESSURE

(75) Inventors: Josef X. Brunner, Chur (CH); Stephan H. Böhm, Lauenburg/Elbe (DE)

(73) Assignee: SWISSTOM AG (CH)

( * ) Notice: Subject to any disclaimer, the term of this patent is extended or adjusted under 35 U.S.C. 154(b) by 529 days.

(21) Appl. No.: 13/508,971

(22) PCT Filed: Oct. 26, 2010

(86) PCT No.: PCT/CH2010/000269
§ 371 (c)(1),
(2), (4) Date: May 9, 2012

(87) PCT Pub. No.: WO2011/054117
PCT Pub. Date: May 12, 2011

(65) Prior Publication Data
US 2012/0232411 A1    Sep. 13, 2012

(30) Foreign Application Priority Data
Nov. 9, 2009 (CH) .................................. 1722/09

(51) Int. Cl.
*G01L 7/08* (2006.01)
*A61B 5/087* (2006.01)
(Continued)

(52) U.S. Cl.
CPC .............. *A61B 5/0876* (2013.01); *G01F 1/383* (2013.01); *A61B 2562/0247* (2013.01); *G01L 7/00* (2013.01)

(58) Field of Classification Search
CPC ............ G01L 7/00; A61B 5/021; A61B 5/031
USPC .......... 73/700, 715; 600/485, 501; 128/205.25
See application file for complete search history.

(56) References Cited

U.S. PATENT DOCUMENTS 3,559,488 A * 2/1971 Weaver .......................... 73/720
4,083,245 A * 4/1978 Osborn ...................... 73/861.53
(Continued)

FOREIGN PATENT DOCUMENTS

WO    WO 02/056768 A1    7/2002

*Primary Examiner* — Lisa Caputo
*Assistant Examiner* — Nigel Plumb
(74) *Attorney, Agent, or Firm* — Morriss O'Bryant Compagni, PC

(57) ABSTRACT

A pressure measuring System (11, 111, 211) is described comprising a sensor assembly (13, 113, 213) and a vessel adapter (17, 217), with the sensor assembly defining a compartment (19, 119, 219, 220), comprising a measurement port (29, 129, 229, 230), an actuator (21, 121, 221, 222) for enabling and disabling pressure transmission across the measurement port, and at least one pressure sensor (23, 123, 223, 224, 225) for measuring a pressure in the compartment relative to a reference pressure, and the vessel adapter defining a fluid chamber (47, 247, 248), said chamber being in pressure connection with the compartment by means of said measurement port, and characterized in that in-between the compartment and the fluid chamber at least one membrane (15, 215) is located which separates the medium in the compartment from the medium in the fluid chamber. The pressure measuring System is used to measure the pressure of a medium in a vessel adapter relative to a reference pressure. In a further embodiment the pressure measuring System is adapted to measure the differential pressure of a medium flowing through a vessel adapter with a flow restrictor.

17 Claims, 10 Drawing Sheets

(51) Int. Cl.
*G01F 1/38* (2006.01)
*G01L 7/00* (2006.01)

(56) References Cited

U.S. PATENT DOCUMENTS

| | | | |
|---|---|---|---|
| 4,180,187 A * | 12/1979 | Ben-Haim | 222/326 |
| 4,787,627 A * | 11/1988 | Daubenspeck | 482/13 |
| 4,971,063 A * | 11/1990 | Flachslaender et al. | 600/490 |
| 5,006,114 A * | 4/1991 | Rogers et al. | 604/245 |
| 5,178,182 A * | 1/1993 | Kamen | 137/454.2 |
| 5,419,509 A * | 5/1995 | Krayenhagen | 242/419 |
| 5,692,497 A * | 12/1997 | Schnitzer et al. | 128/204.21 |
| 7,185,652 B2 * | 3/2007 | Gunaratnam et al. | 128/205.25 |
| 7,282,032 B2 * | 10/2007 | Miller | 600/538 |
| 7,654,146 B2 * | 2/2010 | Orr et al. | 73/700 |
| 2004/0249300 A1 | 12/2004 | Miller | |
| 2007/0225612 A1* | 9/2007 | Mace et al. | 600/532 |
| 2007/0261498 A1 | 11/2007 | Orr et al. | |

* cited by examiner

PRESSURE MEASURING SYSTEM, PRESSURE MEASURING SENSOR ASSEMBLY AND A METHOD OF MEASURING A PRESSURE

CROSS-REFERENCE TO RELATED APPLICATIONS

This application claims priority to Swiss Patent Application Serial No. 1722109 filed on Nov. 9, 2009 and International Application Number PCT/CH2010/000269, filed on Oct. 26, 2010, the entirety of each of which is incorporated by this reference.

BACKGROUND

1. Technical Field

This invention relates to a pressure measuring system, a pressure measuring sensor assembly, a vessel adapter, a ventilator system, a blood pressure measuring system and a method for measuring pressure.

2. Background

Flow and pressure of air in the lungs are important data for intensive care ventilators and anesthesia machines. In fact, monitoring of these parameters is mandated by the pertinent standards today. There is consent among the experts that measurement directly at the airway opening is the best way to measure. However, water vapor condensation, mucus, blood, and possibly other body fluids as well as infectious agents may be present in the airway tubing and present a serious threat to reliable and accurate measurement and patient safety. For this reason, most intensive care ventilators and anesthesia machines measure within the machine and not at the airway opening of patients. On-airway sensing is available only on a few intensive care ventilators. These devices connect the airways to the internal sensors by means of sensing tubes and thus allow "remote" sensing of airway pressure and differential pressure, for example across a flow-measuring restrictor, as disclosed in for example U.S. Pat. No. 4,083,245. The reasons for using sensing tubes are two-fold: first, the pressure sensors need periodic baseline resets and the necessary valves are too heavy to be put at the airways; therefore they are located within the ventilator or anesthesia machine. Second, the relatively long tubes provide a certain separation between airways and the device, thereby protecting the pressure sensors within device from moisture and contamination with bacteria and viruses. However, protection from contamination is not complete and water vapour can easily move into the sensing tubes by means of diffusion. For this reason, a continuous or sporadic purge of the sensing tubes is necessary.

While the state-of-the-art is working well, it has a number of disadvantages: the sensing tubes are prone to kinking and disconnection, the purge flows interrupt the measurement process and introduce measurement errors and thus need to be checked regularly, disconnection of sensing tubes is difficult to monitor by the ventilator or the anesthesia machine and is a safety concern, and contamination of the sensors is not completely avoided if the purge flows stop—for example if the ventilator or the anesthesia machine is stored with the tubing still attached. Finally, the response time of the ventilator or the anesthesia machine is degraded by long sensing tubes and this limits the rapid response to breathing efforts of the patient, for example in Automatic Tube Compensation. Such limitation may be so strong that spontaneous breathing becomes impossible if the patient is very weak, and this in turn will lead to longer time on the ventilator with associated risks for infection, complications and death. US patent application US 2007/0261498 A1 discloses a respiratory pressure sensing system which consists of an airway adapter ("pneumotach") and a pressure transducer. The transducer is designed to receive a respiratory sample when it is coupled with the airway adapter. This system is configured to be coupled directly, without long tubes between said two system components. Pressure ports of the transducer are in gas flow communication with the airway adapter conduit. And consequently during pressure measurement the differential pressure sensor is in direct contact with the respiratory air in the airway conduit. It is suggested to use filters such as hydrophobic, antimicrobial filter materials, e.g. in the form of felt or particles, to prevent microorganisms, moisture, and other contaminants from passing through the coupling ports into conduits of the reusable transducer. However, the filters proposed in said document are gas permeable, in fact they shall not substantially restrict the flow of sampled respiratory gases through pressure ports. Thus contaminated patient air still may reach transducer parts and therefore diminish its reusability. Further protection of pressure or flow transducers is, thus, desirable. For the reasons described above, there is a clear need for a sensor system providing higher patient safety and higher measurement reliability. At the same time costs of such a system should be low.

SUMMARY OF THE INVENTION

The present invention provides a pressure measuring system, a pressure measuring sensor assembly according, a vessel adapter, a ventilator system, a blood pressure measuring system and a method for measuring pressure.

The inventive pressure measuring system is based on a media separating membrane, which allows separation of a pressure measuring sensor assembly from the medium of which the pressure is measured. In a first embodiment the inventive pressure measuring system comprising a sensor assembly and a vessel adapter, with the sensor assembly defining a compartment, comprising a measurement port,
an actuator for enabling and disabling pressure transmission across (i.e. via) the measurement port, and
at least one pressure sensor for measuring a pressure in the compartment relative to a reference,
and
the vessel adapter defining a fluid chamber, said chamber being in pressure connection with the compartment by means of said measurement port
the actuator is mechanically operable (i.e. the actuator is a mechanical actuator),
and
in-between the compartment and the fluid chamber at least one membrane is located which separates the medium in the compartment from the medium in the fluid chamber.

Advantageously in a mounted arrangement of the sensor assembly and the vessel adapter, the medium-separating membrane separates said media. Thus, a media exchange via the measurement port is prevented by the membrane. The membrane therefore is a sealing means with regard to liquid and/or gas, in particular air and/or blood. At the same time the membrane is also a barrier for solid particles and microorganisms, such as e.g. bacteria and viruses.

The membrane is media impermeable, in particular gas and/or liquid impermeable. The membrane consists of a plastic material in form of a foil, for example of a polyester foil, which is attached to the airway adapter by means of glue or a thermal bonding. The membrane has a thickness of 4 to 50 micrometer, 5 to 30 micrometer or 10 to 25 micrometer. At the position of a measurement counter port the membrane forms a protuberance. This is an excess of material exceeding the size that is necessary to bridge the counter port opening. This excess of material may also be described as for example protrusion, nose, projection or dilation. The membrane material is soft and flexible, consequently the protuberance is floppy (unless filled with pressurized gas or liquid). Thus, the mounted media-separating impermeable membrane is floppy and hence called floppy membrane. The protuberance (herein also called protrusion, nose, projection or dilation) of the floppy membrane has a surface area (i.e. surface size) that exceeds the size of the cross section (i.e. cross section size) of the opening of the measurement port by at least 10 percent, while the cross section (e.g. the diameter) of said protuberance, protrusion, nose, projection or dilation is of about the same size as the cross section (e.g. the diameter) of the measurement port. Advantageously the size of the surface (i.e. the expanse or curved surface) of the protuberance exceeds the size of the cross section of the opening area of the measurement port by at least 50 percent, by at least 100 percent, by more than 200 or even more than 500 percent. The membrane, more particularly the protuberance, protrusion, nose, projection or dilation of the membrane, is substantially expansion-free deflectable. By using such a membrane in the inventive measuring system loss of pressure propagation is avoided.

The membrane is media impermeable or can be considered media impermeable for the short time the measurement procedure takes. This requirement warrants accuracy of measurement and prevents contamination of the sensor assembly with substances such as bacteria or viruses contained within the medium in the vessel adapter. Specifically said membrane is impermeable to air, water and blood. A specific membrane is considered impermeable for the purpose of this invention, if during the time frame of a measurement essentially no gas or water may permeate. Meaning that a specific membrane is considered impermeable, if during the time frame of a pressure measurement gas or liquid permeation may not be detected for said membrane within useful accuracy of the measurement. It is advantageous that the pressure measurement error based on gas or liquid permeation is below 1 percent, below 0.1 percent, below 0.01 percent or below 0.001 percent.

Filters typically employed in respiratory conduits, e.g. such as the filters disclosed in US 2007/0261498 A1, serve to retain moisture, microorganisms and other contaminants. These filters, however, do not prevent exchange of respiratory gases. In fact the materials disclosed in said document allow gas exchange between airway adapter conduit and transducer conduits.

The vessel adapter comprises a measurement counter port which is covered by the membrane. Advantageously the membrane is affixed on the vessel adapter. The combination of a vessel adapter and a membrane affixed thereto can be used as a disposable product.

The sensor is adapted to measure the pressure relative to atmosphere.

Advantageously the sensor assembly and the vessel adapter comprise fixation means for mutual releasable fixation, in particular a releasable clip system. A sensor assembly which is not contaminated during use may be reused. The releasable fixation allows easy removal of the sensor assembly from the vessel adapter. The actuator is formed and arranged to deflate the protuberance. The actuator employed is for example a mechanical actuator in the form of a piston, a lever or a stamp or in the form of a piston, a lever or a stamp with a pusher end designed as a cylinder, a disk, a balloon or a soft ball for pushing the protuberance out of the chamber and at the same time closing the measurement port. The actuator is mechanically movable and thus mechanically operable. The actuator is designed to push back or deflate a membrane protruding into the compartment of the sensor assembly. Advantageously, the actuator is designed not to damage or penetrate the membrane material of the protuberance, thus for example having an edgeless or blunt pusher end.

The measurement port in the compartment and the measurement counter port in the vessel adapter are aligned face-to-face. Alternatively, the measurement port in the compartment and the measurement counter port in the vessel adapter are connected by means of a connecting tube which forms a pressure connection.

The actuator is arranged such that it closes in a first position the measurement port, i.e. disables pressure transmission across the measurement port, and opens in a second position the measurement port, i.e. enables pressure transmission across the measurement port. Hereby, the measurement port remains always sealed by means of the impermeable and floppy membrane. Thus, the opening and closing of the measurement port by pushing the actuator against the port opening and retracting the actuator from the port opening, respectively, is understood as an enabling and disabling of pressure transmission across the measurement port without actually allowing media exchange and mixing, e.g. media such as gas or liquid.

The actuator is situated within the compartment of the sensor assembly. In particular the pusher end is situated within the compartment.

Advantageously the compartment comprises a release port and a valve means for closing and opening said release port. The release port opens the compartment to a reference pressure, for example to atmosphere. The advantageous effect of the integration of said release port with valve function consists in the possibility of resetting the chamber pressure to reference pressure conditions before starting a measurement of the pressure in the vessel adapter. As a side effect of the resetting action the general functioning of the sensor and actuator can be checked. Unlike the measurement port, the release port is not sealed.

Advantageously the measurement port and the release port can be opened and closed by the same activator. A valve means is mounted onto the actuator in such a manner that the valve means is able in a first position to close the release port and in a second position to open the release port. In use measurement port and release port need to be opened or closed independently from each other. In order to fulfill this requirement two separate actuators may be arranged in the compartment, whereby each actuator performs the opening and closing of one of the two ports. Advantageously, an alternative actuator means is arranged in the compartment, which is adapted to perform the opening and closing of both ports. Such an actuator—comprising both functionalities—comprises a pusher and a valve means. Whereby the pusher is adapted for closing the measurement port and manipulating the membrane and the valve means is adapted for opening and closing the release port. Advantageously, pusher and closing valve means, each situated on a common lever, are independent from each other axially movable to close and/or open the measurement port and/or release port. For example the pusher is situated on one end of the lever and the closing valve means in the form of for example a valve head is situated on said same lever in axial distance from the pusher. Hereby the mutual distance of valve means and pusher is controllable.

However, common to any type of activator within the compartment is the requirement that at all positions of the activator, in particular of the pusher, the activator, respectively the pusher, occupies substantially the same volume within the compartment. Thus, this assures that during measurement the major part of the pressure change within the compartment is due to the deflection of the protuberances of the floppy membrane.

In a second embodiment the pressure measuring system comprising a sensor assembly, a vessel adapter and a membrane as described above with said sensor assembly, vessel adapter and membrane comprise the sensor assembly defining two compartments, a first and a second compartment, each compartment comprising a measurement port, and an actuator for opening and closing the respective measurement port, i.e. enabling and disabling pressure transmission across the respective measurement port, whereby at least one pressure sensor is arranged to measure a differential pressure between said two compartments, the vessel adapter defining two fluid chambers, a first and a second fluid chamber, each fluid chamber being in pressure connection with the respective compartment by means of the respective measurement port, and said first fluid chamber and said second fluid chamber being in communication by means of a flow restrictor, the at least one membrane being located in-between the first compartment and the first fluid chamber and in-between the second compartment and the second fluid chamber separating the medium in the first compartment and the medium in the second compartment from the medium in the respective fluid chamber of the vessel adapter.

The second compartment comprising a second measurement port, a second actuator and optionally a second release port showing the same features and advantages as described above with regard to the described first embodiment of the invention.

The at least one membrane is floppy, i.e. forming at least a protuberance, whereby the surface size of each protuberance exceeds the size of the cross section of the opening of the measurement port by at least 10 percent, while the cross section (e.g. the diameter) of each protuberance is of about the same size as the cross section (e.g. the diameter) of the measurement port.

Advantageously, the surface size of each protuberance exceeds the size of the cross section of the opening of the measurement port by at least 50 percent, or by at least 100 percent.

The actuators are formed and arranged to deflate the protuberances.

The pressure sensor is in contact with the first and the second compartment for measuring a differential pressure between said two compartments.

Advantageously, at least one further pressure sensors is arranged in one or both of the compartments for measuring the pressure relative to a reference pressure, for example atmospheric pressure. The mechanical actuators are in the form of pistons, levers or stamps or in the form of pistons, levers or stamps with a pusher end designed as a cylinder, a disk, a balloon or a soft ball. Each of said measurement ports is covered by the at least one membrane. The measurement ports in the compartments are aligned face-to-face with the measurement counter ports in the vessel adapters. Advantageously, the actuators close in a first position the measurement ports and open in a second position the measurement ports. More advantageously, each compartment comprises a release port and a valve means for closing and opening said release port.

Advantageously, the sensor assembly and the vessel adapter comprise fixation means for mutual releasable fixation, in particular a releasable clip system. The inventive pressure measuring sensor assembly comprising a compartment equipped with at least a measurement port, an actuator for opening and closing the measurement port, and a pressure sensor for measuring a pressure in the compartment relative to a reference pressure, whereby said compartment is adapted to be mounted on a vessel adaptor defining a fluid chamber, which is designed for being in pressure connection with the compartment by means of said measurement port, wherein the actuator is mechanically operable (i.e. the actuator is a mechanical actuator).

The actuator is in the form of a piston, a lever or a stamp and or in the form of a piston, a lever or a stamp with a pusher end designed as a cylinder, a disk, a balloon or a soft ball. The actuator is adapted to close in a first position the measurement port and open in a second position the measurement port.

Optionally, the compartment comprises a release port and a valve means for closing and opening said release port.

Advantageously the sensor is arranged to measure the pressure relative to a reference pressure, relative to atmospheric pressure.

In a further embodiment the inventive pressure measuring sensor assembly comprises two compartments whereby said compartments are adapted to be mounted on a vessel adapter defining two fluid chambers, which are designed for being in pressure connection with the compartments by means of measurement ports, and at least one pressure sensor is arranged to measure a differential pressure between said two compartments. The at least one pressure sensor is in contact with the first and the second compartment for measuring a differential pressure between said two compartments.

Advantageously, further pressure sensors are arranged in one or both of the compartments for measuring the pressure relative to atmosphere.

The mechanical actuators are in the form of pistons, levers or stamps or in the form of pistons, levers or stamps with a pusher end de-signed as a cylinder, a disk, a balloon or a soft ball.

The actuators are adapted to close in a first position the measurement ports and open in a second position the measurement ports.

Optionally, each compartment comprises a release port and a valve means for closing and opening said release port.

Optionally, the sensor assembly comprises fixation means for releasable fixation on said vessel adapter, in particular a releasable dip system.

The inventive vessel adapter, in particular the inventive airway adapter, comprises a mounting surface adapted to receive a sensor assembly as defined above.

The vessel adapter comprises at least one measurement counter port which is covered by a membrane, which is suitable for retaining a medium within the vessel adapter and transmitting pressure to a sensor.

Advantageously, the membrane is floppy, i.e. forming a protuberance, whereby the surface size of the protuberance exceeds the size of the cross section of the opening of the measurement port by at least 10 percent, while the cross section (e.g. the diameter) of the protuberance is of about the same size as the cross section (e.g. the diameter) of the measurement port.

The surface size of the protuberance exceeds the size of the cross section of the opening of the measurement port by at least 50 percent, or by at least 100 percent.

The inventive ventilator system comprises a pressure measuring system as defined above.

The inventive method for measuring the pressure of a medium in a vessel adapter uses a sensor assembly that is mounted on said vessel adapter, said vessel adapter having a chamber, said sensor assembly comprising a compartment having at least a pressure sensor, a measurement port, mechanically operating actuator and optionally a release port, said compartment being in pressure connection with said chamber by means of said measurement port, and a membrane being interposed between said compartment and said chamber with said membrane forming a protuberance, and comprises the steps of a) optionally, opening the release port to set the pressure in the compartment to ambient pressure, b) setting the actuator to a first position and thereby pushing the protuberance into a starting position and closing the measurement port, c) optionally measuring baseline pressure data, d) if open, closing the release port, e) retracting the actuator to a second position and thereby releasing the protuberance and opening the measurement port to equalize the pressure in the compartment with the pressure in the vessel adapter chamber, and f) computing pressure data and optionally comparing with baseline pressure data.

Hereby, opening the measurement port means that the actuator is retracted to allow pressure equalization between chamber and compartment, and closing the measurement port means that the actuator is pushed against the opening of the measurement port in order to disable pressure equalization between chamber and compartment.

The inventive method for measuring the differential pressure of a medium flowing through a vessel adapter uses a sensor assembly that is mounted on said vessel adapter, said vessel adapter defining a first and a second fluid chamber, and said chambers being mutually connected via a flow restrictor, said sensor assembly comprising a first and a second compartment, said compartments being separated by a differential pressure sensor, each of said compartments further having a measurement port, a mechanically operating actuator and optionally a release port, each of said compartments being in pressure connection with one respective chamber by means of said measurement ports, and a membrane being interposed between said compartments and said respective chambers with said membrane forming at least two respective protuberances, comprises the steps of a) optionally, opening the release ports to set the pressure in the compartments to ambient pressure, b) setting the actuators to a first position and thereby pushing the protuberances into a starting position and closing the measurement ports, c) optionally, measuring baseline pressure data, d) if open, closing the release ports, e) retracting the actuators to a second position and thereby releasing the protuberances and opening the measurement ports to equalize the pressure in the compartments with the pressure in the respective vessel adapter chambers, and f) computing pressure data and optionally comparing with baseline pressure data.

Hereby, opening the measurement port means that the actuators are retracted to allow pressure equalization between chambers and respective compartments, and closing the measurement port means that the actuators are pushed against the opening 15 of the measurement port in order to disable pressure equalization between chambers and compartments.

With the inventive system the pressure within a vessel adapter relative to a reference pressure, for example atmospheric pressure, can be determined. Also the pressure difference across a flow restrictor located within a vessel adapter or flow duct, for example an airway adaptor, can be measured with the inventive system. The sensor assembly is described in two different embodiments. First, a basic assembly allows the measurement of a pressure relative to a reference point such as atmosphere. This first sensor assembly consists of one compartment. Second, a more sophisticated assembly allows the measurement of a differential pressure. This second sensor assembly consists of two pneumatically separated compartments. Common to both assembly embodiments is that each compartment is equipped with a measurement port and optionally a release port. The release port opens to a reference pressure, for example to atmosphere, and the measurement port opens to connect to a vessel adapter. The vessel adapter is equipped with one measurement counter port when used with the first sensor assembly variant and with two measurement counter ports when used with the second sensor assembly variant. Each measurement port can be equipped with at least one mechanical actuator in each compartment. This actuator can be a piston, a lever or a stamp. In order to manipulate the position of the floppy membrane of the airway adapter, the mechanical activator is formed as a piston within a cylinder. In another embodiment, the mechanical activator can be a disk with small holes to push the floppy membrane into position and at the same time to allow equilibration of pressures around the sealing portion of the sensor assembly. In yet another embodiment the mechanical activator is a balloon which is inflated by an external pump or an external gas source. In yet another embodiment, the mechanical activator is a soft ball that pushes the floppy membrane gently into position. Each release port can be opened and closed by a valve mechanism. valve mechanism is an electrically driven piston with seal, for example a valve head fixed on a lever, that closes the opening to ambient pressure. Typical sealing pressures for measuring airway pressures are 30 hPa, but can be as high as 120 hPa. For measuring arterial blood pressures, these sealing pressures will be considerably higher as high as 300 mmHg. The valve mechanism and the pusher mechanism are individually controllable.

The vessel adapter comprises one or respectively two measurement counter ports which are covered by a floppy membrane. The sensor assembly connects to the measurement counter port or measurement counter ports and contains o-rings or other means to seal each passage from a measurement port to its measurement counter port from ambient. If two passages are formed the two passages are sealed from each other. Once the sensor assembly is connected to the vessel adapter the valves and the mechanical actuator within the sensor assembly perform the following actions:

a) Optionally, the valve within each compartment is activated to open the respective release port to ambient pressure, b) the mechanical actuator of each compartment is activated to push the respective floppy membrane of the vessel adapter into a starting position and close the respective measurement port, c) optionally, the valve within each compartment is activated to close the respective release port, and d) the mechanical actuator of each compartment is activated to release the respective floppy membrane of the vessel adapter by opening the respective measurement port.

The purpose of actions a and b is to achieve a reliable mechanical baseline reset as follows:

step a serves to pneumatically connect each pressure sensor to a common reference point, i.e. ambient pressure, and step b serves to eliminate pressure influence from the vessel adapter by mechanically positioning the floppy membrane to a deflated start position.

Once steps a and b are executed, the baseline of all pressure sensors can be reliably measured and compensated in later measurements.

The purpose of steps c and d are to pneumatically connect the sensor assembly with the vessel adapter and, more precisely, to transmit the pressures within the vessel adapter or each vessel adapter chamber to the sensor or each sensor within the sensor assembly:

after execution of step c each compartment is closed and ready to be pressurized;

after execution of step d each compartment equilibrates with the corresponding pressure of the vessel adapter chamber.

Once the steps c and d are executed, the floppy membranes are to a certain extent but essentially without strain inflated and protrude into the compartments. The pressures on both sides of the floppy membrane are identical, and therefore the pressure sensor or if applicable the pressure sensors within the sensor assembly measure the pressure within the vessel adapter or within each chamber of the vessel adapter, respectively.

All the measurements, readings, and actions of the sensor assembly are controlled entirely or in part by a microprocessor within the sensor assembly. The results are being transmitted via a cable to an external device for display and/or displayed on a display attached to the sensor assembly. Optionally, the measurements, readings, and actions of the sensor assembly are controlled entirely or in part by a microprocessor outside the sensor assembly. The results are being transmitted via a cable to an external device for display. In yet another embodiment, the data is transferred wirelessly, for example by radio frequency or infrared light.

Ambient pressure means atmospheric pressure or any other reference pressure to which ambient conditions are set.

In the following the present invention is described with reference to specific figures and embodiments.

DETAILED DESCRIPTION

Pressure Measurement Relative to a Given Ambient Pressure

Figure 1:
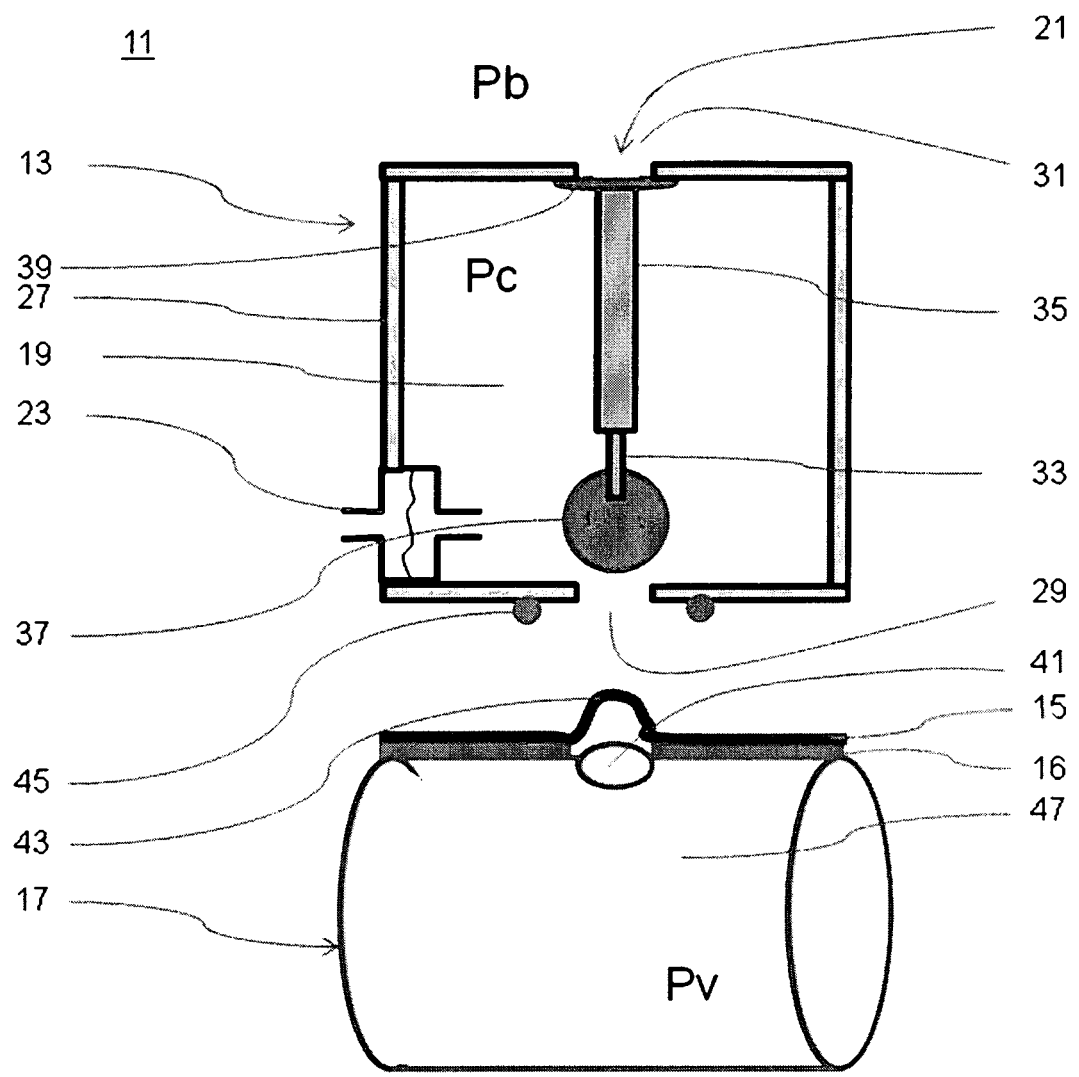
FIG. 1: Pressure measuring system comprising a sensor assembly and a membrane covered airway adapter, wherein the sensor assembly comprises a compartment with an actuator and a pressure sensor.

FIGS. 1 to 5 show a first embodiment of a pressure measuring system 11 comprising a sensor assembly 13 and a membrane 15 covered vessel adapter 17. In FIG. 1 sensor assembly 13 and membrane 15 covered vessel adapter 17 are presented in a disconnected arrangement. The sensor assembly 13 comprises a compartment 19 with an actuator 21 and a pressure sensor 23. The pressure sensor 23 is arranged on or integrated in a side wall 27 of the compartment. In this way the sensor is able to measure the pressure in the compartment 19 relative to the given ambient pressure outside the compartment. The compartment 19 comprises two openings, a measurement port 29 and a release port 31. The actuator 21 consists of a pusher 33 and a stem 35. The pusher 33 is equipped with a pusher head 37. The stem 35 is equipped with a valve means 39. Pusher 33 and stem 35 of the actuator 21 are movably connected to each other. Pusher 33 and stem 35, thus the entire actuator 21, are axially movably mounted. Hereby pusher 33 and stem 35 are movable independently from each other. Pusher 33, pusher head 37, valve means 39 and stem 35 are arranged within the compartment 19. In a first position the pusher head 37 is positioned in a short distance from the measurement port 29 (FIGS. 1, 2 and 5), such that the measurement port 29 is open. The pusher 33 is extendable in axial direction. After movement towards the measurement port 29 the pusher head 37 hermetically closes the measurement port 29 in a second position (for example in FIG. 3 or 4). Around the measurement port 29 and between the compartment 19 and the vessel adapter 17 a seal, for example an o-ring 45, is provided in order to seal the passageway between the compartment 19 and the vessel adapter 17, in particular its chamber 47. The valve means 39 closes the release port 31 in a first position hermetically (FIGS. 1, 2, 4 and 5). In a second position the valve means 39 is repositioned into the compartment 19 in order to leave the release port 31 open (see FIG. 3). The actuator 21 comprises a motors (not shown here) allowing the herein described movements and is affixed to the compartment walls 27 via an adequate anchorage (not shown here).

The vessel adapter 17 comprises a measurement counter port 41. This port 41 is covered with a membrane 15. A support 16 may be affixed in-between the membrane 15 and the vessel adapter 17. The membrane 15 is floppy and forms a protuberance 43, which is easily deflectable by a liquid or gaseous medium like air or blood. The membrane 15 consists of an airtight material. Optionally, the membrane 15 is also expandable to a certain extent.

For use the sensor assembly 13 is mounted onto the vessel adapter 17, in such a way that the measurement port 29 of the sensor assembly 13 and the measurement counter port 41 of the adapter 17 are aligned in a face-to-face position (see FIGS. 2-5). The 0-ring 45 is squeezed in-between the sensor assembly 13 and the membrane 15 covered vessel adapter 17 forming an air-tight contact of the two system parts. The media within the adapter 17 and the compartment 19 are media-separated by the membrane 15. But at the same time pressure communication is warranted via said floppy membrane 15. The force necessary to squeeze the o-ring 45 is applied via a clip mechanism (not shown here), which holds the sensor assembly in unmovable and airtight contact with the vessel adapter 17.

Before or after the sensor assembly 13 is mounted and dipped onto the adapter 17, said adapter is integrated into a pipe system where the pressure measurement takes place. According to one example the adaptor 17 is integrated into a lung ventilation tubing for a patient. In another example the adaptor 17 may be connected to a catheter leading to a blood vessel for direct blood pressure measurement. In both applications the media volume is very different. Thus, size and volume of the adapter 17 and the sensor assembly 13 need to be chosen with regard to the specific application.

Figure 2:
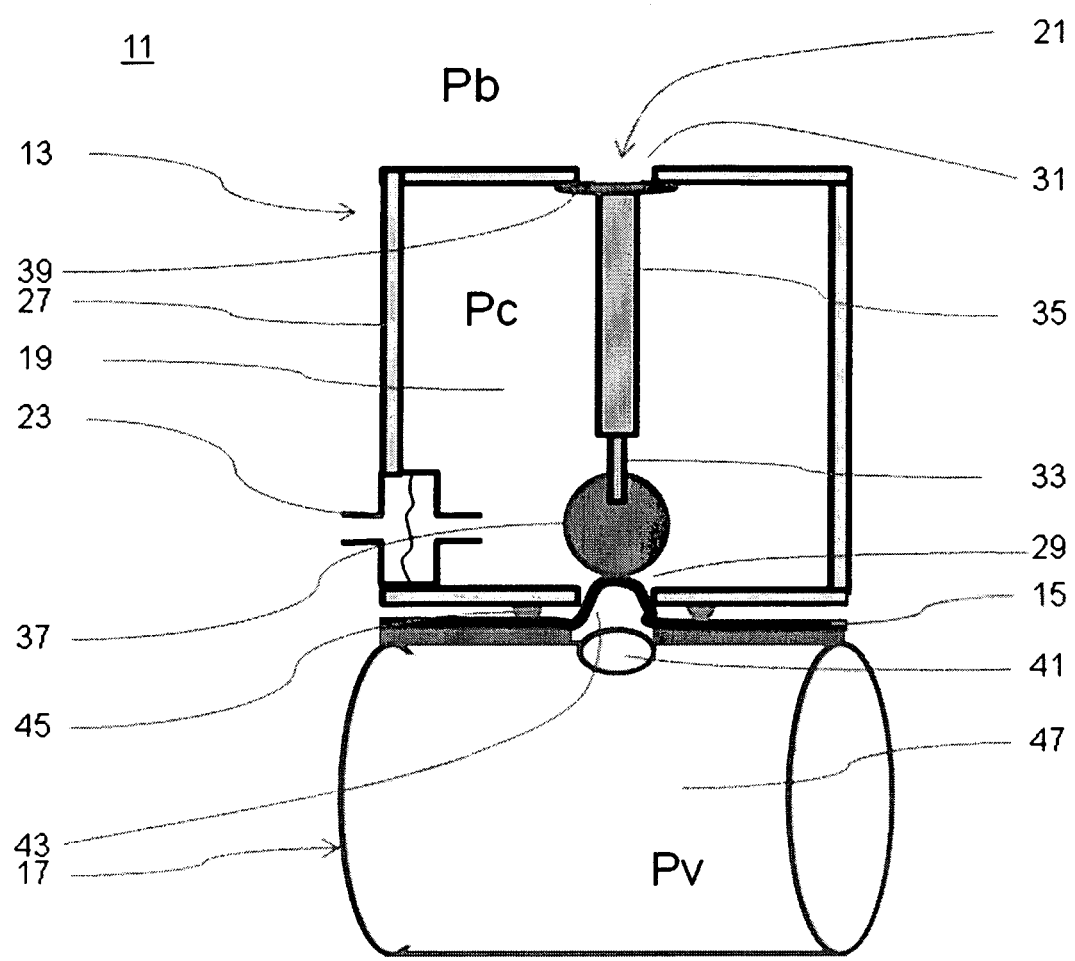
FIG. 2: Mounted pressure measuring system comprising a sensor assembly clipped onto a membrane covered airway adapter.

Operation of the inventive pressure measuring system 11 is demonstrated with reference to FIGS. 2 to 5. In FIG. 2 the sensor assembly 13 is mounted and fixed onto the vessel adapter 17 (which previously was already integrated into a to be examined tubing system such as a lung ventilation tubing). The membrane 15 is press fitted between vessel adapter 17 and sensor assembly 13. The base of the protuberance 43 of the membrane 15 is situated in the passage between measurement port 29 and measurement counter port 41.

Once the pressure measuring system 11 is set up as indicated in FIG. 2, the sequence of operation may be started.

Figure 3:
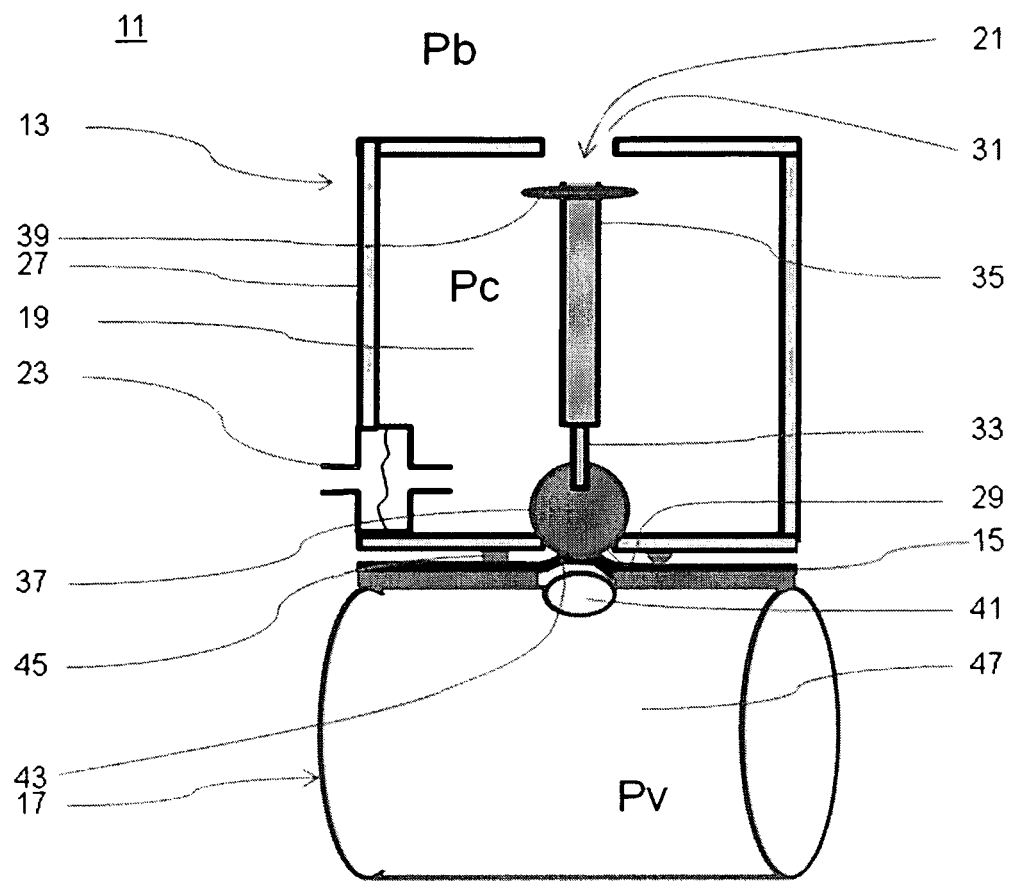
FIG. 3: Pressure measuring system of FIG. 2 in reset position.

As indicated in FIGS. 2 and 3, the pusher head 37 is moved against the measurement port 29 in order to close the opening air-tight. Movement of the pusher head 37 is achieved by activating the pusher 33 only (when pusher 33 and stem 35 are decoupled) or the whole activator 21 (when pusher 33 and stem 35 are coupled). Due to the movement of the pusher head 37 the protuberance 43 is squeezed or pushed out of the compartment 19. At the same time or thereafter the stem 35 with the valve means 39 is lowered into the compartment 19 for opening the release port 31. At the position as given in FIG. 3, with the pusher head 37 closing the measurement port 29 and the valve means 39 removed from the release port 31, the pressure (Pc) in the measuring compartment 19 is equalized with the ambient pressure, for example atmospheric pressure (Pb).

Figure 4:
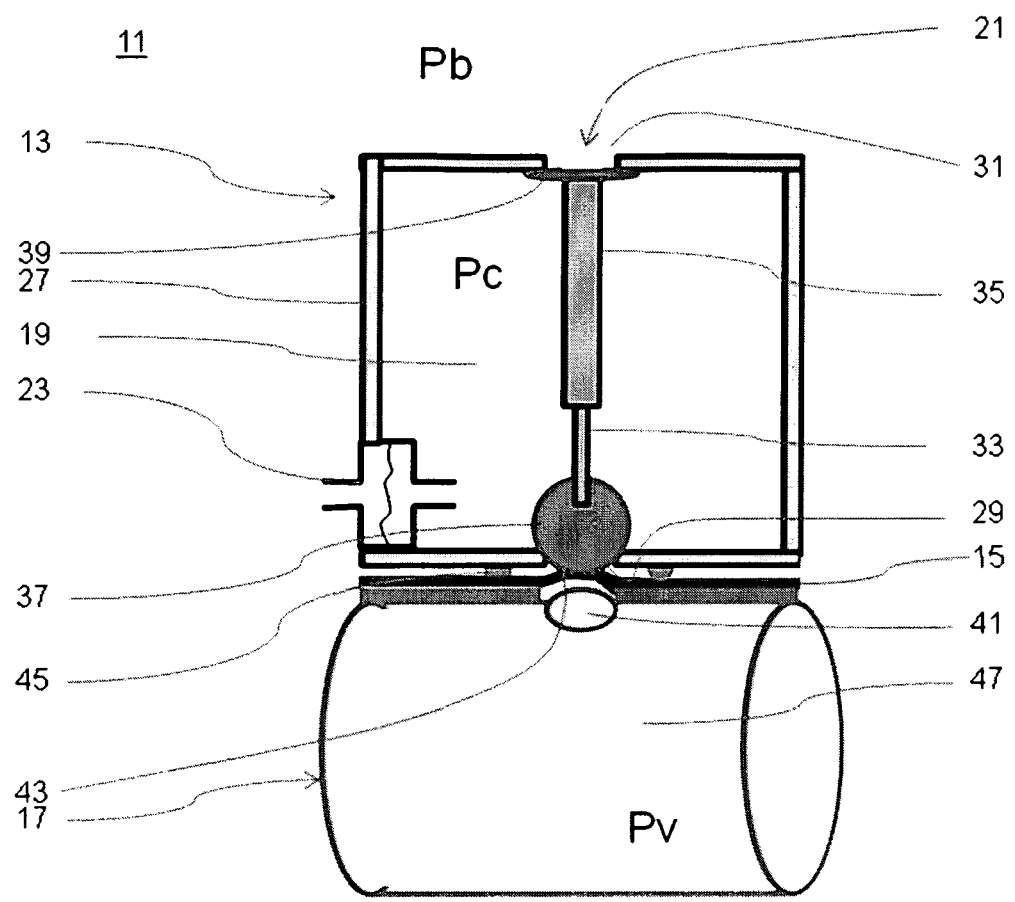
FIG. 4: Pressure measuring system of FIG. 2 in intermediate position.

As indicated in FIG. 4, the release port 31 is closed by moving stem 35 and valve means 39 in axial direction against the release port 31. Hereby the stem 35 and valve means 39 are decoupled from pusher 33 and pusher head 37. Thus while stem 35 and valve means 39 are moved, pusher 33 and pusher head 37 remain at their closing position. At the position as given in FIG. 4, with the pusher head 37 closing the measurement port 29 and the valve means 39 closing the release port 31, the pressure (Pc) in the measuring compartment 19 is maintained at ambient pressure, for example atmospheric pressure (Pb).

Figure 5:
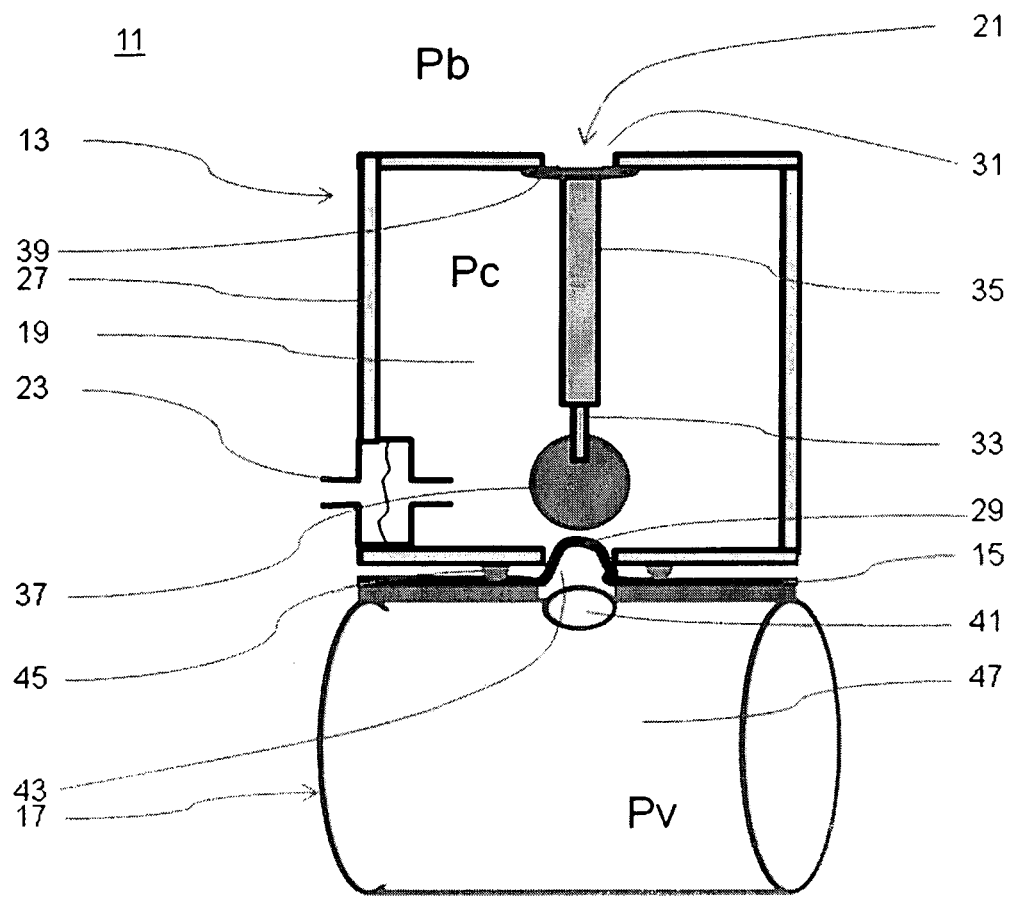
FIG. 5: Pressure measuring system of FIG. 2 in measuring position.

In FIG. 5 the actual measurement is executed by retracting the pusher head 37 from the measurement port 29 to free said port 29, while the release port 31 is kept closed. Once the measurement port 29 is open, the protuberance 43 may—depending on the pressure (Pv) in the vessel adapter 17—to a certain extent deflect and protrude into compartment 19. The membrane protuberance 43 needs to be designed in a size large enough in order to be able to fully transmit the overpressure in the adapter vessel 17 into the compartment 19. At the position as given in FIG. 5, with the pusher head 37 removed from the measurement port 29 and the valve means closing the release port 31, the pressure (Pc) in the measuring compartment 19 is equalized with the pressure (Pv) in the vessel adapter. A data processor connected to the pressure sensor 23 stores the measured pressure data.

By moving the pusher head 37 against the measurement port 29 in order to close the opening again, the measurement sequence may be started anew.

In summary the measurement operation comprises at least the following steps:
 1. closing of measurement port 29 and opening release port 31, simultaneously or sequentially;
 2. closing release port 31; and
 3. opening measurement port 29, and
 4. reading of the measured pressure data of sensor 23.

This sequence may be repeated in order to measure time dependent behavior.

With the described system a pressure value relative to ambient may be determined. A pressure value relative to atmospheric pressure is determined. Thus an absolute pressure value for the examined medium results from said measurement.

In use the vessel adapter 17 is integrated into a pipe or tubing system or is arranged in communicating contact with a container, whose interior pressure shall be measured. Said pipe, tubing system or container may carry a gaseous or liquid medium. This includes suspensions. In one example the vessel adapter 17 is flooded with blood. In order to measure the blood pressure the adapter is integrated into a tubing system that is in communication with the blood circulation system of a patient.

Figure 6:
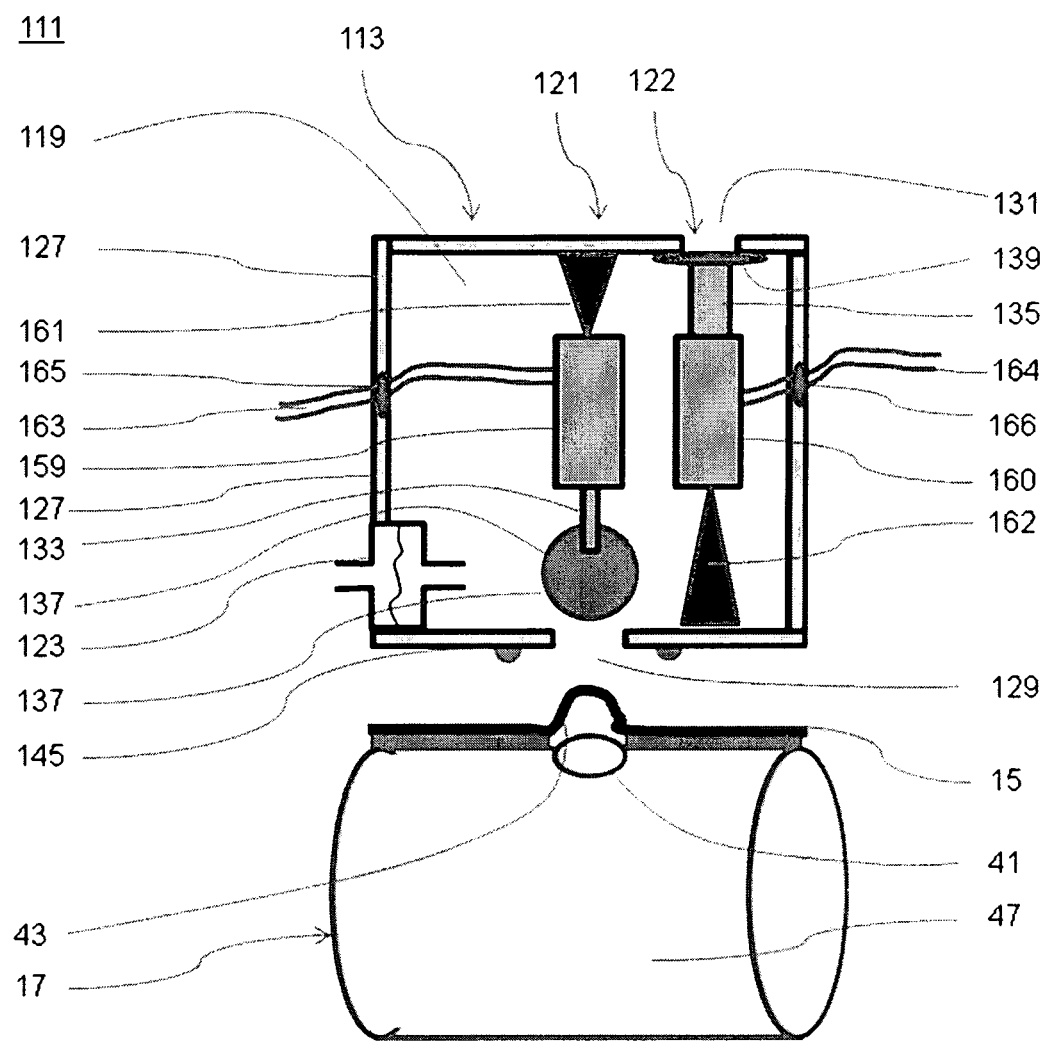
FIG. 6: Pressure measuring system comprising a sensor assembly and a membrane covered airway adapter, wherein the sensor assembly comprises a compartment with two actuators and a pressure sensor.

In FIG. 6 there is presented a pressure measuring system 111 with an alternative pressure measuring sensor assembly 113. This sensor assembly 113 is mountable onto the membrane 15 covered vessel adapter 17 as described above. Similarly to the above described sensor assembly 13, this sensor assembly 113 comprises at least one pressure sensor 123 which is able to measure the pressure in the compartment 119 relative to the given ambient pressure outside the compartment 119. Hereto the pressure sensor 123 is arranged on or integrated in a side wall 127 of the compartment 119. Furthermore, the compartment 119 comprises two openings, a measurement port 129 and a release port 131. Each opening is opened and closed by a respective actuator. The first actuator 121 is arranged to open and close the measurement port 129. For this purpose the first actuator 121 consists of a pusher 133 connected to a first motor 159. The first motor 159 and the pusher 133 are arranged and fixed by a first anchorage 261 within chamber 119. The first motor 159 is for example controlled via the activation cable 163, which enters the compartment 119 through a cable feed-through 165 in the side wall 127. Activation cable 163 and cable feed-through 165 form an air-tight seal whereby the cable 163 is unshiftable relative to the feed-through 165. Other electrical contacting arrangements may be envisaged. The pusher 133 comprises a pusher head 137 formed as described above and is axially movably mounted for opening and closing said measurement port 129. Meaning that the pusher head has the functionality of enabling and disabling pressure transmission across said measurement port. The second actuator 122 is arranged to open and close the release port 131. For this purpose the second actuator 122 consists of a valve member 139 connected to a second motor 160. The second motor 160 and the valve member 139 are arranged and fixed by a second anchorage 262 within chamber 119. The second motor 160 is for example controlled via the activation cable 164, which enters the compartment 119 through a cable feed-through 166 in the side wall 127. Activation cable 164 and cable feed-through 166 form an air-tight seal whereby the cable 164 is unshiftable relative to the feed-through 166. Other electrical contacting arrangements may be envisaged. The valve member 139 is fixed on a stem 135. The stem 135 is axially movably mounted for opening and closing said release port 131.

Thus differing from the above first described sensor assembly 13, this alternative sensor assembly 113 comprises two actuators, a first actuator 121 and a second actuator 122, within the compartment 119. The above initially described actuator 21 combines two functionalities: the opening and closing of the measurement port 29 and the opening and closing of the release port 31 (FIGS. 1 to 5). In the alternative sensor assembly 113 these two functionalities are separated and first and second functionality are executed by the first and second actuators 121 and 122, respectively (FIG. 6).

Differential Pressure Measurement

Figure 7:
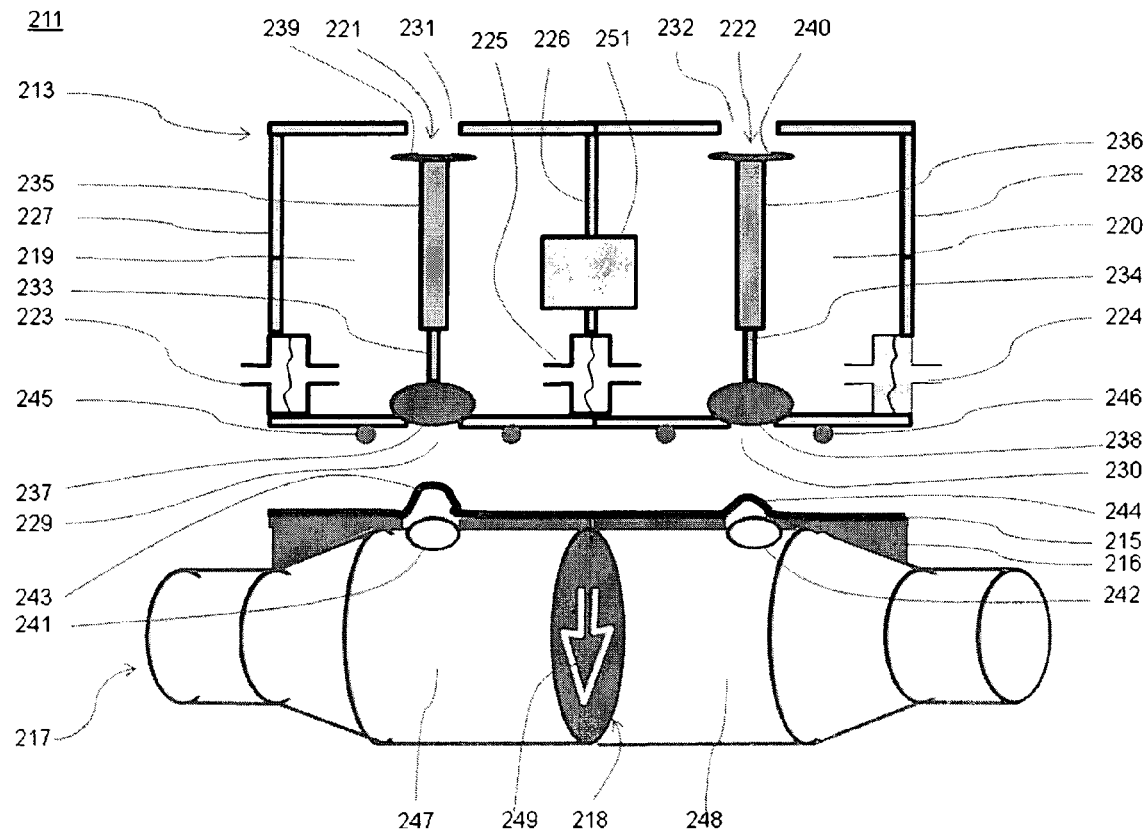
FIG. 7: Pressure measuring system comprising a sensor assembly and a membrane covered airway adapter, wherein the sensor assembly forms two compartments equipped with a common pressure sensor and in each single compartment equipped with an actuator and a further pressure sensor, and further comprising a position sensor.
Figure 8:
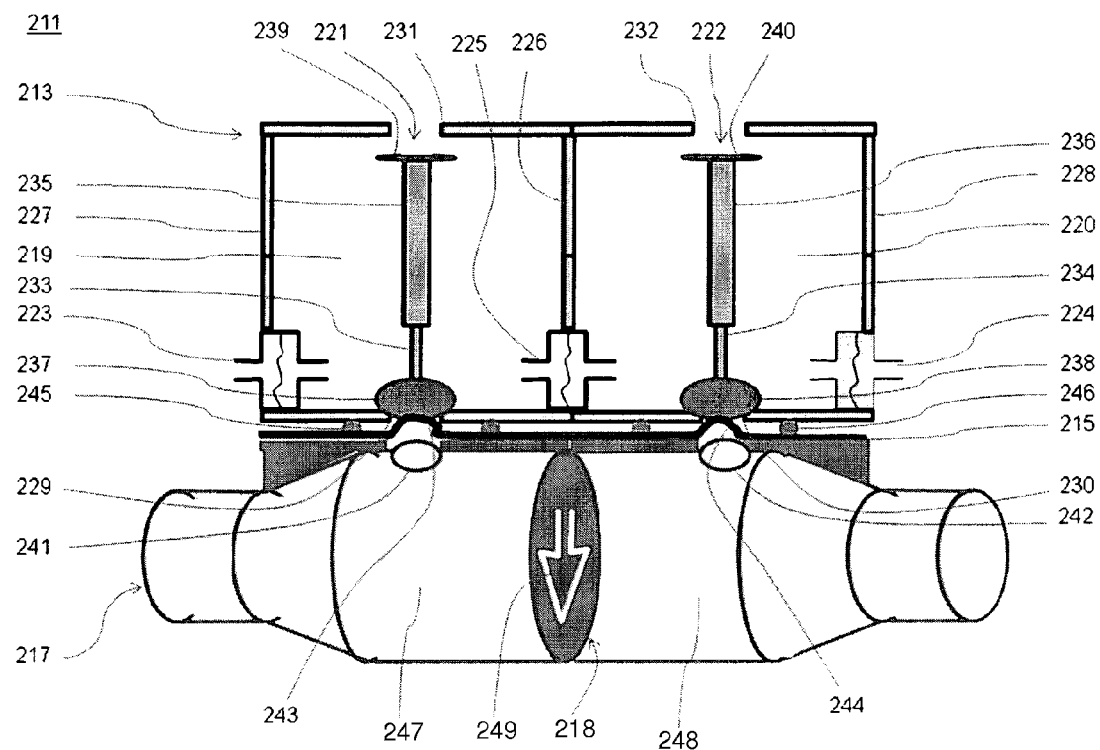
FIG. 8: Pressure measuring system of FIG. 7 mounted and in reset position.
Figure 9:
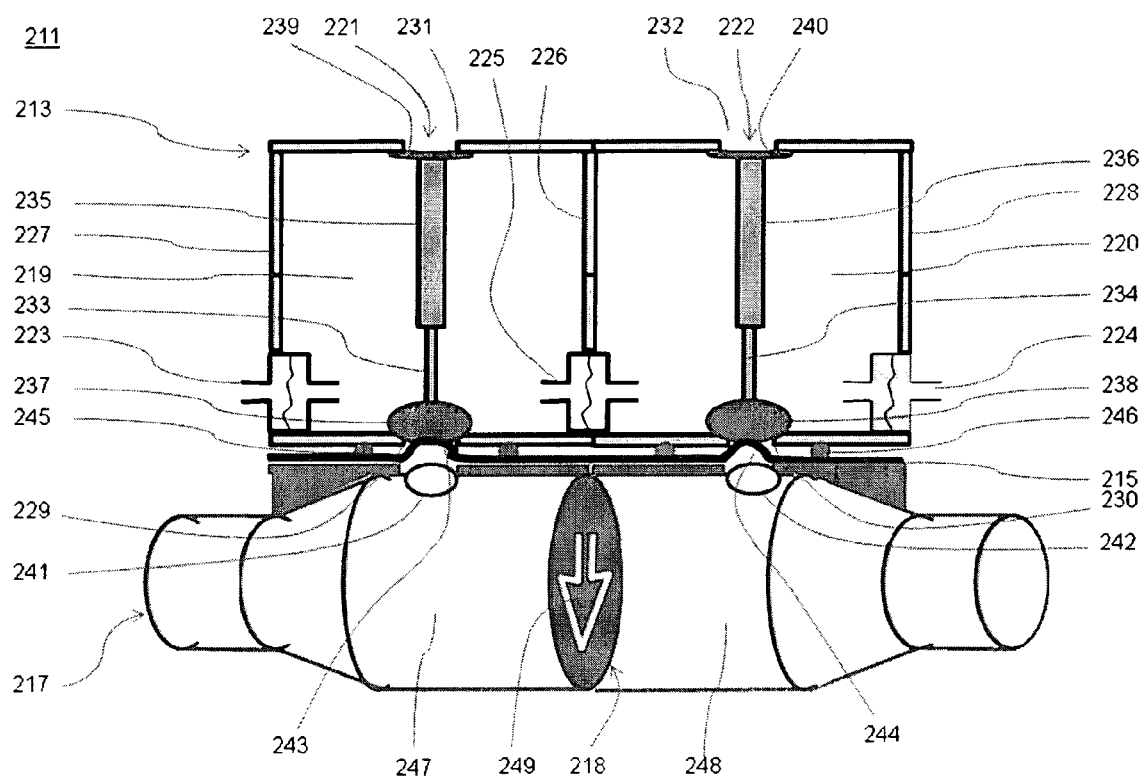
FIG. 9: Pressure measuring system of FIG. 7 mounted and in intermediate position.
Figure 10:
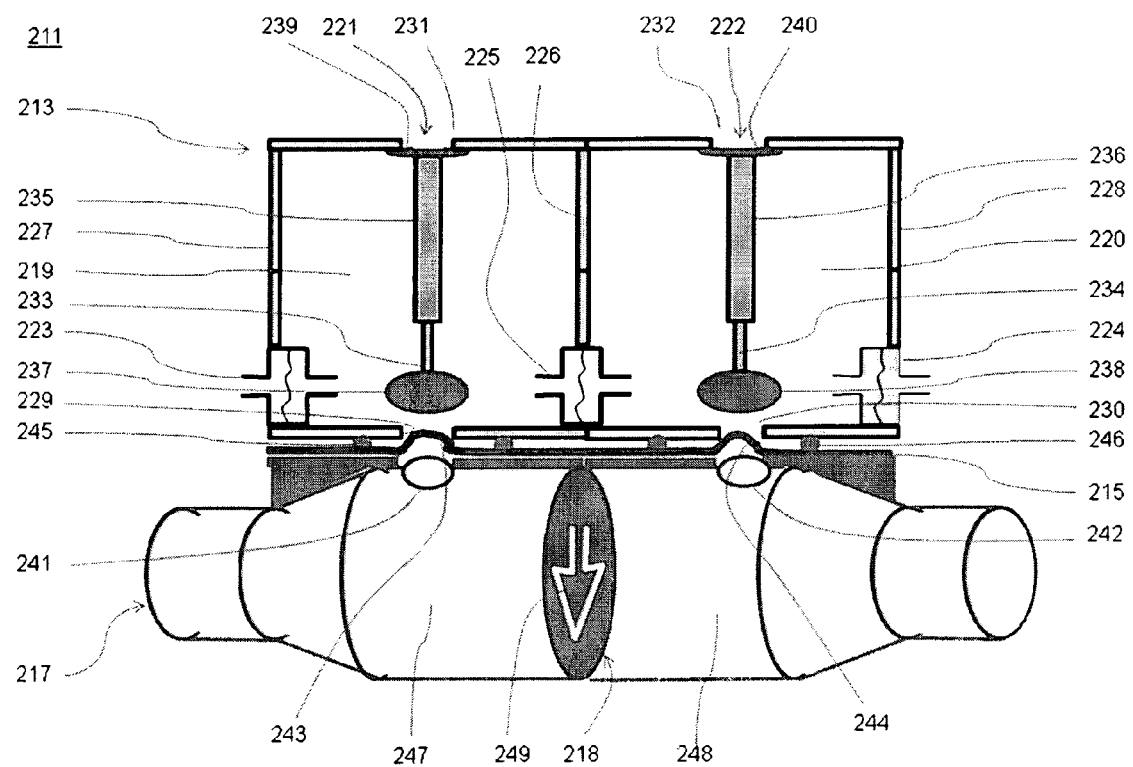
FIG. 10: Pressure measuring system of FIG. 7 mounted and in measuring position.

In a second embodiment FIGS. 7 to 10 show a pressure measuring system 211 comprising a sensor assembly 213 and a membrane 215 covered vessel adapter 217. The vessel adapter 217 comprises a flow restrictor 218. In FIG. 7 sensor assembly 213 and membrane 215 covered vessel adapter 217 are presented in a disconnected arrangement. The sensor assembly 213 comprises two compartments, a first compartment 219 and a second compartment 220, each equipped with an actuator, first actuator 221 and second actuator 222, and two pressure sensors (such as gauge pressure sensors), i.e. at least a first pressure sensor 223 and optionally a second pressure sensor 224. The pressure sensors 223 and 224 are integrated into respective side walls 227 and 228 of the compartments. The two compartments 219 and 220 are separated by a separation wall 226. A third pressure sensor 225 is integrated into the separation wall 226. The sensors 223 and 224, that are mounted to the side walls 227 and 228, are able to measure the pressure within the compartments 219 and 220 relative to the given ambient pressure outside the compartment. The pressure sensor 225, which is mounted to the separation wall, does measure the differential pressure between the two compartments 219 and 220. Furthermore, each of the compartments 219 and 220 comprises two openings, a first measurement port 229 and a first release port 231 and a second measurement port 230 and a second release port 232. The actuators 221 and 222 consist each of a pusher 233 and 234 and a stem 235 and 236, respectively. The pushers 233 and 234 are equipped with pusher heads 237 and 238. The stems 235 and 236 are equipped with valve means 239 and 240. Pushers 233 and 234 and stems 235 and 236 of the actuators 221 and 222 are movably connected. Pushers 233 and 234, stems 235 and 236, and the entire actuators 221 and 222 are axially movably mounted. Hereby pushers 233 and 234 and stems 235 and 236 are movable independently from each other. Pushers 233 and 234 and pusher heads 237 and 238 are received in respective compartments 219 and 220, such that in a first position the pusher heads 237 and 238 are positioned in a distance from the respective measurement ports 229 and 230 (FIG. 10). The measurement ports 229 and 230 are thus open. The pushers 233 and 234 are extendable in axial direction, such that the pusher heads 237 and 238 close the respective measurement ports 229 and 230 in a second position hermetically (e.g. FIGS. 7, 8 and 9). The valve means 239 and 240 hermetically close the release ports 231 and 232 in a first position (FIGS. 9 and 10). In a second position the valve means 239 and 240 are repositioned within the respective compartments 219 and 220 in order to leave the respective release ports 231 and 232 open (FIGS. 7 and 8). Around the measurement ports 229 and 230 are situated two sealings, e.g. o-rings 245 and 246. The actuators 221 and 222 comprise motors (not shown here) allowing the herein described movements and are affixed to the compartment walls (227 and/or 228) via an anchorage (not shown here).

The vessel adapter 217 comprises a flow restrictor 218 and two measurement counter ports 241 and 242, whereby the flow restrictor 218 is arranged in-between the two ports 241 and 242 separating the vessel adapter into two chambers 247 and 248. The flow restrictor 218 is equipped with a variable orifice, in particular a hinged flap 249. The measurement counter ports 241 and 242 are covered with a membrane 215. A support 216 may be affixed in-between the membrane 215 and the vessel adapter 217. The membrane 215 is floppy and forms protuberances 243 and 244, which are easily deflectable by a liquid or gaseous medium like air or blood. The deflection occurs without any resistance. The membrane 215 consists of an airtight material. Optionally, the membrane 215 is also expandable to a certain extent.

For use the sensor assembly 213 is mounted onto the vessel adapter 217, in such a way that the first and second measurement ports 229 and 230 of the sensor assembly 213 and the respective first and second measurement counter ports 241 and 242 of the vessel adapter 217 are aligned in a face-to-face position (see FIGS. 8-10). The o-rings 245 are squeezed in-between the sensor assembly 213 and the membrane 215 covered vessel adapter 217 forming an air-tight contact of the two system parts. The force necessary to squeeze the o-ring 245 is applied via a clip mechanism (not shown here), which holds the sensor assembly in unmovable and air-tight contact with the vessel adapter 217. The media within the adapter 217 and the compartments 219 and 220 are media-separated by the membrane 215. But at the same time pressure communication is warranted via said floppy membrane 215. The media within the two compartments 219 and 220 are also separated from each other. A pressure comparison of the two compartments is achieved by the pressure sensor 225.

Before or after the sensor assembly 213 is mounted and dipped onto the adapter 217, said adapter is integrated into a pipe system where the pressure measurement takes place. According to one example the adaptor 217 is integrated into a lung ventilation tubing for a patient.

Operation of the inventive pressure measuring system 211 is demonstrated with reference to FIGS. 8 to 10. In FIG. 8 the sensor assembly 213 is mounted and fixed onto the vessel adapter 217 (which previously was already integrated into a to be examined tubing system such as a lung ventilation tubing). The membrane 215 is press fitted between vessel adapter 217 and sensor assembly 213. The origin of the protuberances 243 and 244 of the membrane 215 is situated in the passage between measurement ports 229 and 230 and respective measurement counter ports 241 and 242.

Once the pressure measuring system 211 is set up as indicated in FIG. 8, the sequence of operation may be started.

As indicated in FIG. 8, the pusher heads 237 and 238 are pressed against their respective measurement ports 229 and 230 in order to close the opening in an air-tight manner. At the same time the pusher heads 237 and 238 push the protuberances 243 and 245 out of the respective compartments 219. At the same time the stems 235 and 236 with the valve means 239 and 240 are lowered into the respective compartments 219 and 220 with respect to the release ports 231 and 232. At the position as given in FIG. 8, with the pusher heads 237 and 238 closing the measurement ports 229 and 230 and the valve means 239 and 240 removed from the release ports 231 and 232, the pressures (Pel and Pc2) in the measuring compartments 219 and 220 are equalized with the ambient pressure, for example atmospheric pressure (Pb).

As indicated in FIG. 9, the release ports 231 and 232 are closed by moving stems 235 and 236 and valve means 239 and 240 in axial direction against the respective release ports 231 and 232. Hereby the stems 235 and 236 and valve means 239 and 240 are decoupled from respective pushers 233 and 234 and pusher heads 237 and 238. Thus while stems 235 and 236 and valve means 239 and 240 are moved, pushers 233 and 234 and pusher heads 237 and 238 remain at their respective closing positions. At the positions as given in FIG. 9, with the pusher heads 237 and 238 closing the measurement ports 229 and 230 and the valve means 239 and 240 closing the release ports 231 and 232, the pressures (Pe1 and Pc2) in the respective first and second measuring compartments 219 and 220 is maintained at ambient pressure, for example atmospheric pressure (Pb).

In FIG. 10 the actual measurement is executed by retracting the pusher heads 237 and 238 from the measurement ports 229 and 230 to free said ports 229 and 230, while the release ports 231 and 232 are kept closed. Once the measurement ports 229 and 230 are open, the protuberances 243 and 244 may—depending on the pressure (Pv) in the vessel adapter 217—to a certain extent deflect and protrude into compartments 219 or protrude into vessel adapter 217. The membrane protuberances 243 and 244 need to be designed in a size large enough in order to be able to fully transmit the pressure in the chambers 247 and 248 of the adapter vessel 217 into the respective compartments 219 and 220. At the position as given in FIG. 10, with the pusher heads 237 and 238 removed from the measurement ports 229 and 230 and the valve means 239 and 240 closing the release ports 231 and 232, the pressures (Pe1 and Pc2) in the measuring compartments 219 and 220 are equalized with the pressure (Pv1 and Pv2) in the respective vessel adapters. A data processor connected to the pressure sensor 225 stores the measured differential pressure data and allows further computation of a flow. Optionally, the readings of the gauge pressure sensors 223 and 224 may be compared to calculate a differential pressure and a flow. This value could be compared with the reading of the differential pressure sensor 225 in order to check the proper functioning of the sensors.

By moving the pusher heads 237 and 238 against the respective measurement ports 229 and 230 in order to close the opening again, the measurement sequence may be started anew.

In summary the measurement operation comprises the following steps:
1. closing of measurement ports 229 and 230 and opening release ports 231 and 232, simultaneously or sequentially,
2. closing release port 231,
3. opening measurement port 229, and
4. reading of the measured pressure data of sensor 225.

This sequence may be repeated in order to measure time dependent behavior. Optionally with step 2 and step 4, measured data of sensors 223 and/or 224 may be read and compared with the previous readings of the same sensors in order to determine if sensor and activator are reacting and thus are functioning.

With the described system a differential pressure value is determined.

In use the vessel adapter 217 is integrated into a pipe or tubing system. The determined differential pressure may be related to a flow. Said pipe or tubing system carries a gaseous or liquid medium. This includes suspensions. In one example the vessel adapter 217 is an airway adapter. In order to measure the pressure of air in a ventilation tube the airway adapter is integrated into the ventilation tubing of a patient.

Description of Use when Measuring Airway Pressure

A typical application is the combined measurement of airway pressure and airway gas flow in an intensive care ventilator or an anesthesia machine. The purpose is to monitor and control the gas flow to and from the patient. In this use, the airway adapter connects the ventilator or anesthesia machine with the endotracheal tube of the patient. The airway adapter is typically a single patient use device, possibly made of transparent plastics. It can be envisioned that it is made of autoclavable material. The results of any measurement, performed as disclosed below, are displayed on the intensive care ventilator, the anesthesia machine or at the site of the airway adapter.

In this use, the sensor assembly 213 contains two pressure measuring ports 229 and 230, each leading to a respective compartment 219 and 220, see FIG. 7. The airway adapter 217 contains two pressure measuring counter ports 241 and 242 and one flow restrictor 218 arranged in-between the two ports 241 and 242 (FIG. 7). The purpose of the sensor assembly is to measure the pressure with respect to atmosphere (airway pressure) and the pressure drop across the flow restrictor. The latter provides a measurement of gas flow within the airways.

Before or after the airway adapter 217 is connected with the patient, the sensor assembly 213 is clipped onto the airway adapter 217. Thereafter, the sequence of valve opening and closing is executed as described above, the baseline is reset, and the measurements can start. Periodically, the baseline reset can be repeated without manual intervention and without disturbing the flow of gas to and from the patient.

Since the pressure sensors measure right at the airway openings 241 and 242, any control of gas flow and pressure by the ventilator or anesthesia machine can be made very fast using this invention. Furthermore, monitoring of sensing tubes, purge flow, and kinking of tubes is no more necessary and replaced by a simple check of electrical connection. Additionally, the valve mechanism, consisting of release ports 231 and 232 and valve means 239 and 240 on the mechanical actuators 221 and 222, within the sensor assembly 213 can be used to check proper operation of the sensor assembly 213 periodically by opening the release ports 231 and 232 to atmosphere and measuring with the descriptive pressure sensors 223 and 224 the associated change in pressure. If a pressure change is absent, then possibly either at least one actuator 221 or 222 or at least one respective pressure sensor 223 or 224 is not working. Such continuous check of operation increases the safety of intensive care ventilators and anesthesia machines and reduces false positive alarms.

In another use, the inventive pressure measuring system is used independent of an intensive care or emergency ventilator or anesthesia machine. In this case, the inventive pressure measuring system is connected to a display unit that shows the results of the measurements as graph, waveform, number or a combination thereof. Alternatively, a display may be provided on the sensor assembly. The display unit may further provide alarm thresholds and alert the user with audible and visual signals in case one or several of these thresholds are exceeded. There are thousands of intensive care ventilators, still in use and properly operating, which do not comply with current regulations since they lack monitoring of exhaled air. The purpose of such a standalone unit is to add monitoring of exhaled flow and pressure to existing and already installed ventilators and anesthesia machines.

Although the sensor assembly 213 is protected against contamination with patient mucus, blood, infectious agents etc., the sensor assembly 213 is supposed to sit on top of the airway adapter 217 to avoid the collection of water, blood, mucus, or saliva on the floppy membrane 215. Any material on the floppy membrane 215 might de-crease the measurement bandwidth. To avoid such unfavorable position, a position sensor 251 is integrated into the sensor assembly 213. Hereby the position sensor 251 is integrated in the central separating wall 226 of the sensor assembly 213 (FIG. 7). However, the position sensor 251 may be attached or integrated at any position where the functioning of the sensor is not constrained by its presence, in particular where the actuator or actuators are not constrained in their movement. The position is periodically read by an attached microprocessor and a user message is generated to alert the clinician in case the sensor assembly is in the wrong position.

To enhance the precision of the measurements and to eliminate production variations of the airway adapter 217, the airway adapter 217 may be pre-calibrated and the calibration constants may be imprinted on the airway adapter 217. This calibration information 253 is placed onto the surface of the airway adapter in such a way that it can be read out by a reader 255 within the sensor assembly 213. For example, the calibration information 253 may consist of a binary code burned onto the surface of the air-way adapter. In another embodiment, a Radio Frequency Identification (RFID) chip may be glued to the airway adapter and read by an RFID reader within the sensor assembly. In yet another embodiment, each airway adapter is labeled with a bar code and a bar code reader is integrated into the sensor assembly.

In the following there are given further exemplary details with regard to specific system components such as airway adapter, sensor assembly and more particularly membrane, actuator, sensor, pre-calibration and microprocessor:

In another embodiment, the disclosed invention consists of two parts, an airway adapter and a sensor assembly. The airway adapter contains a flow restrictor, a variable orifice, for example a flap, and two pressure measuring counter ports which are sealed against ambient air and against each other by means of a gas impermeable and floppy membrane. For example, a polyester foil which is attached to the airway adapter by means of glue or a thermal bonding can be used. The airway adapter connects to the endotracheal tube or a patient mask on one side, and to the ventilator tubing or anesthesia machine tubing on the other side. Pertinent information about the diameters are given in the ISO standards and apply.

The sensor assembly is divided into two hermetically, sealed compartments. Each compartment has a mechanical activator or lever, operated by an electromechanical component, which is used to manipulate the position of the floppy membrane of the airway adapter. The mechanical lever can be a piston within a cylinder. In another embodiment, the mechanical lever can be a disk with small holes to push the floppy membrane into position and at the same time to allow equilibration of pressures around the sealing portion of the sensor assembly. In yet another embodiment the mechanical lever is a balloon which is inflated by an external pump or an external gas source. In yet another embodiment, the mechanical lever is a soft ball that pushes the floppy membrane gently into position.

Each compartment has one opening to ambient which can be closed with a valve. The valve is a simple electrically driven piston with seal that closes the opening to ambient. Typical sealing pressures for measuring airway pressures are 30 hPa, but can be as high as 120 hPa. For measuring arterial blood pressures, these sealing pressures will be considerably higher as high as 300 mmHg. The valve may be a component of the actuator.

The pressure difference between the two compartments is measured by means of a pressure differential transducer. A typical range of pressure is +/−3 hPa. The pressure difference to ambient of at least one compartment is measured with a second pressure differential transducer. In another embodiment, both compartments are fitted with a pressure differential sensor to ambient, one serving as backup for the other. In one embodiment, the acoustic and pneumatic impedance (transient response to pressure step) of both compartments are matched. This is primarily done by matching the gas volume of both compartments and avoiding sub-compartments within each compartment.

Although the sensor assembly is protected against contamination with for example patient mucus, blood, infectious agents etc., the sensor assembly is supposed to sit on top of the vessel adapter to avoid the collection of water, blood, mucus, or saliva on the floppy membrane. Any material on the floppy membrane might decrease the measurement bandwidth. To avoid such unfavorable position, a position sensor is integrated into the sensor assembly. The position sensor is integrated in a convenient position of the sensor assembly. The position is periodically read by an attached microprocessor and a user message is generated to alert the clinician in case the sensor assembly is in the wrong position.

To enhance the precision of the measurements and to eliminate production variations of the airway adapter, the airway adapter may be pre-calibrated.

The present invention, in particular the second embodiment, can be used as a stand-alone pneumotachograph for lung function testing in a pulmonary function lab or as a screening tool in a general physicians practice. It can also be used to measure pressure and flow in respiratory assist devices, intensive care ventilators, home care ventilators, and emergency ventilators. A further use is in anesthesia machines. Yet another use is in vital signs monitors to monitor flow, pressures, inspired volumes and expired volumes of air, and other respiratory parameters. Yet another use is in ventilatory support devices for closed-loop control of respiratory gas delivery, pressure delivery, or breath delivery in general. Such use includes but is not limited to intensive care or emergency ventilators, home care ventilators, and anesthesia machines.

Although the present invention has been described in considerable detail and with reference to certain versions thereof, other versions are possible. Therefore, the spirit and scope of the appended claims should not be limited to the description of the versions or embodiments contained therein. Any element in a claim that does not explicitly state "means for" performing a specified function, or "step for" performing a specified function, is not to be interpreted as "means" or "step" clause.

The reader's attention is directed to all papers and documents which are filed concurrently with his specification and which are open to public inspection with this specification, and the contents of all such papers and documents are incorporated herein by reference. All features disclosed in this specification (including any accompanying claims, abstract, and drawings) may be replaced by alternative features serving the same, equivalent or similar purpose, unless expressly stated otherwise. Unless expressly stated otherwise, each feature disclosed is one example only of a generic series of equivalent or similar features.

The invention claimed is:
1. A pressure measuring system, comprising:
a sensor assembly defining a first compartment, the first compartment comprising a measurement port, a mechanical actuator for enabling and disabling pressure transmission across the measurement port, a release port and a valve for closing and opening the release port, and at least one pressure sensor for measuring a pressure in the first compartment relative to a reference pressure;

a vessel adapter defining a first fluid chamber, the first fluid chamber being in pressurized connection with the first compartment by the measurement port; and at least one membrane that separates a first medium in the first compartment from a second medium in the first fluid chamber, the at least one membrane located between the first compartment and the first fluid chamber, and the at least one membrane forming a protuberance, the mechanical actuator configured and arranged to deflate the protuberance and close the measurement port at the same time.

2. The pressure measuring system of claim 1, wherein a surface area of the protuberance exceeds the cross sectional area of the opening of the measurement port by at least 10 percent to 100 percent.

3. The pressure measuring system of claim 1, wherein the mechanical actuator is comprised of one of a piston, a lever or a stamp with a pusher end configured as one of a cylinder, a disk, a balloon or a soft ball.

4. The pressure measuring system of claim 1, wherein the vessel adapter comprises a measurement counter port that is covered by the membrane.

5. The pressure measuring system of claim 1, wherein the mechanical actuator is configured to move from a first position to a second position and to disable pressure transmission across the measurement port when the mechanical actuator is in the first position and enable pressure transmission across the measurement port when the actuator is in the second position.

6. The pressure measuring system of claim 1, wherein the sensor is configured to measure the pressure relative to atmospheric pressure.

7. The pressure measuring system of claim 1, wherein the sensor assembly and the vessel adapter further comprise a releasable clip system for mutual releasable fixation.

8. The pressure measuring system of claim 1, wherein the sensor assembly defines a second compartment, the first and second compartments each comprising a measurement port, a mechanical actuator for enabling and disabling pressure transmission across the respective measurement port, with the at least one pressure sensor being configured to measure a differential pressure between the first and second compartments, wherein the vessel adapter defines a second fluid chamber, the first and second fluid chambers being in pressure connection with a respective first and second compartment by a respective measurement port, said first fluid chamber and said second fluid chamber being in communication by a flow restrictor, and wherein the at least one membrane is located between the first compartment and the first fluid chamber and between the second compartment and the second fluid chamber, separating the medium in the first compartment and the medium in the second compartment from the medium in the respective fluid chamber of the vessel adapter, the at least one membrane forming at least two respective protuberances.

9. The pressure measuring system of claim 8, wherein the at least one pressure sensor is in contact with the first and the second compartments for measuring a differential pressure between the first and second compartments.

10. The pressure measuring system of claim 9, further comprising at least one additional pressure sensor arranged in one of the first and second compartments for measuring pressure therein relative to atmosphere.

11. The pressure measuring system of claim 1, wherein the sensor assembly, the vessel adapter and the at least one membrane are configured to operate with a ventilator.

12. The pressure measuring system of claim 1, wherein the sensor assembly, the vessel adapter and the at least one membrane are configured to operate with a blood pressure measuring system.

13. A method for measuring the pressure of a medium in a vessel adapter relative to a reference pressure, comprising:

using a sensor assembly mounted on a vessel adapter, the vessel adapter comprising a chamber, the sensor assembly comprising a compartment having at least one pressure sensor, a measurement port and a mechanical actuator, a release port and a valve for closing and opening the release port, the compartment being in pressure connection with the chamber by the measurement port, and a membrane interposed between the compartment and the chamber with the membrane forming a protuberance opening the release port to set the pressure in the compartment to ambient pressure;

setting the actuator to a first position thereby pushing the protuberance into a starting position and disabling pressure transmission across the measurement port;

closing the release port;

retracting the actuator to a second position, thereby releasing the protuberance and enabling pressure transmission across the measurement port to equalize the pressure in the compartment with the pressure in the vessel adapter chamber; and computing pressure data.

14. The method of claim 13, further comprising measuring baseline pressure data and comparing the computed pressure data with the baseline pressure data.

15. A method for measuring the differential pressure of a medium flowing through a vessel adapter, comprising:

using a sensor assembly mounted on a vessel adapter, the vessel adapter comprising a first and a second fluid chamber, the first and second fluid chambers being mutually connected via a flow restrictor, the sensor assembly comprising a first and a second compartment, the first and second compartments being separated by a differential pressure sensor, each of the first and second compartments further comprising a measurement port and a mechanical actuator, a release port and a valve for closing and opening the release port, each of said first and second compartments being in pressure connection with a respective chamber by the measurement port, and a membrane being interposed between the first and second compartments and the respective first and second chambers with the membrane forming at least two respective protuberances;

opening the release ports to set the pressure in the first and second compartments to ambient pressure;

setting the mechanical actuators of the first and second compartments to a first position thereby deflating the protuberance, pushing each of the at least two protuberances into a starting position and disabling pressure transmission across each of the measurement ports, closing the release ports;

retracting the actuators to a second position thereby releasing the at least two protuberances and enabling pressure transmission across the measurement ports to equalize the pressure in the first and second compartments with the pressure in the respective first and second fluid chambers, and computing pressure.

16. The method of claim 15, further comprising measuring a baseline pressure and comparing the pressure to the baseline pressure.

17. A pressure measuring apparatus, comprising:
a sensor assembly defining a compartment;
a measurement port;
a mechanical actuator configured for opening and closing the measurement port;
a release port;
a valve configured for closing and opening the release port;
at least one pressure sensor for measuring a pressure of a medium in the compartment relative to a reference pressure; and
a media separating membrane providing separation of the at least one pressure sensor from the medium, the membrane sealing the measurement port and forms a protuberance, the actuator configured to deflate the protuberance and close the measurement port at the same time;
whereby the compartment is configured to be mounted on a vessel adaptor defining a fluid chamber, the fluid chamber being in pressure connection with the compartment by the measurement port.

* * * * *